(12) United States Patent
Schwab

(10) Patent No.: US 7,909,854 B2
(45) Date of Patent: Mar. 22, 2011

(54) VARIABLE CONNECTOR

(75) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 496 days.

(21) Appl. No.: 11/742,426

(22) Filed: Apr. 30, 2007

(65) Prior Publication Data

US 2007/0282339 A1     Dec. 6, 2007

Related U.S. Application Data

(60) Provisional application No. 60/795,718, filed on Apr. 29, 2006.

(51) Int. Cl.
*A61B 17/70* (2006.01)
(52) U.S. Cl. .................. 606/250; 606/251; 606/278
(58) Field of Classification Search .......... 606/250–256, 606/260–264, 278–279
See application file for complete search history.

(56) References Cited

U.S. PATENT DOCUMENTS

| 6,811,567 | B2 | 11/2004 | Reiley |
| 2002/0143330 | A1* | 10/2002 | Shluzas ........................... 606/61 |
| 2003/0114853 | A1* | 6/2003 | Burgess et al. ................. 606/61 |
| 2005/0228378 | A1* | 10/2005 | Kalfas et al. .................... 606/61 |

* cited by examiner

*Primary Examiner* — Eduardo C Robert
*Assistant Examiner* — Christina Negrelli

(57) ABSTRACT

A spinal fixation system connector for maintaining a predetermined positions of a spinal linkage members fastened to vertebrae of a patient. The connector includes a body having first and second openings extending along first and second axes, respectively. The connector includes a first fastener for fastening the first member in the first opening and a second fastener for fastening the second member in the second opening. Prior to the first fastener fastening the first spinal linkage member in the first opening and the second fastener fastening the second spinal linkage member in the second opening, the body is manipulatable to adjust an angle between the first axis and the second axis. When the first fastener fastens the first member in the first opening and the second fastener fastens the second member in the second opening, the angle between the first axis and the second axis is fixed.

29 Claims, 4 Drawing Sheets

VARIABLE CONNECTOR

CROSS-REFERENCE TO RELATED APPLICATIONS

This application claims priority from U.S. Provisional Patent Application No. 60/795,718 filed Apr. 29, 2006, which is hereby incorporated by reference.

BACKGROUND

The present invention relates to a spinal fixation system connector for maintaining predetermined positions of vertebrae in the spinal column of a patient. More particularly, the present invention relates to a component of a spinal fixation system for connecting a first spinal linkage member (e.g., a rod) to a second spinal linkage member. The component allows angles between the connected spinal linkage members to vary.

Spinal fixation systems are commonly used to align, adjust and/or stabilize portions of a spinal column of a patient. These systems frequently include vertebral anchors such as pins, bolts, screws, hooks and/or cables that attach to vertebrae in the spinal column. The spinal linkage members can be connected to the anchors to maintain the relative positions of the corresponding vertebrae. Thus, the members maintain the spacing and alignment of the connected vertebrae. To provide desired alignment across several levels of the spine, more than one spinal linkage member may be used and connected by one or more fixation system connectors.

Frequently, the connector is used to connect portions of two linkage members positioned side-by-side. The connector spans between linkage members to maintain the positions of the members relative to each other. Frequently, the portions of the spinal linkage members connected by the connector are not parallel. Instead, the members are non-parallel so they are oriented at various angles and in various positions due to the anatomical structure of the spine and alignment desired by the surgeon.

Many conventional connectors are designed to accommodate linkage members aligned at a particular angle. Variations in angular alignment from the particular angle accepted by the linkage may make it difficult to optimally align members using the conventional connectors. When there is a difference between the desired alignment and the fixed alignment of conventional connectors, the linkage members must be deformed. Deforming members may weaken portions of the spinal fixation system or cause the vertebrae to fail.

BRIEF SUMMARY

The present invention relates to a spinal fixation system connector for maintaining a predetermined position of a first spinal linkage member fastened to vertebrae of a patient to a second spinal linkage member fastened to vertebrae of the patient. The connector comprises a body having a first opening extending through the body along a first axis. The first opening is sized and shaped for receiving the first spinal linkage member. The connector also includes a second opening extending through the body along a second axis. The second opening is sized and shaped for receiving the second spinal linkage member. Further, the connector includes a first fastener mounted on the body for fastening the first spinal linkage member in the first opening of the body and a second fastener mounted on the body for fastening the second spinal linkage member in the second opening of the body. Prior to the first fastener fastening the first spinal linkage member in the first opening of the body and the second fastener fastening the second spinal linkage member in the second opening of the body, the body is manipulatable to adjust an angle between the first axis and the second axis. When the first fastener fastens the first spinal linkage member in the first opening of the body and the second fastener fastens the second spinal linkage member in the second opening of the body, the angle between the first axis and the second axis is fixed.

In another aspect, the invention includes a surgical system for maintaining a predetermined position of vertebrae of a patient. The system comprises a first elongate spinal linkage member, a first anchor for attaching the first member to a first vertebra, a second elongate spinal linkage member, a second anchor for attaching the second member to a second vertebra, and a connector. The connector includes a body having a first opening extending through the body along a first axis. The first opening is sized and shaped for receiving the first spinal linkage member. In addition, the connector includes a second opening extending through the body along a second axis. The second opening is sized and shaped for receiving the second spinal linkage member. The system also comprises a first fastener mounted on the body for fastening the first spinal linkage member in the first opening of the body and a second fastener mounted on the body for fastening the second spinal linkage member in the second opening of the body. Prior to the first fastener fastening the first spinal linkage member in the first opening of the body and the second fastener fastening the second spinal linkage member in the second opening of the body, the body is manipulatable to adjust an angle between the first axis and the second axis. When the first fastener fastens the first spinal linkage member in the first opening of the body and the second fastener fastens the second spinal linkage member in the second opening of the body, the angle between the first axis and the second axis is fixed.

The invention also includes a method of connecting a first spinal linkage member fastened to vertebrae of a patient to a second spinal linkage member fastened to vertebrae of the patient and maintaining a predetermined position of the first spinal linkage member to the second spinal linkage member. The method comprises inserting a portion of the first spinal linkage member into a first opening in the connector and inserting a portion of the second spinal linkage member into a second opening in the connector. The connector is manipulated so the first spinal linkage member and the second spinal linkage member are aligned in a predetermined orientation with respect to one another. The method also includes fastening the connector to the first spinal linkage member and fastening the connector to the second spinal linkage member.

Other aspects of the present invention will be in part apparent and in part pointed out hereinafter.

BRIEF DESCRIPTION OF THE DRAWINGS

Corresponding reference characters indicate corresponding parts throughout the several views of the drawings. Directional terms such as top and side are used for convenience and correspond only to one orientation of the connector.

DETAILED DESCRIPTION

Figure 1:
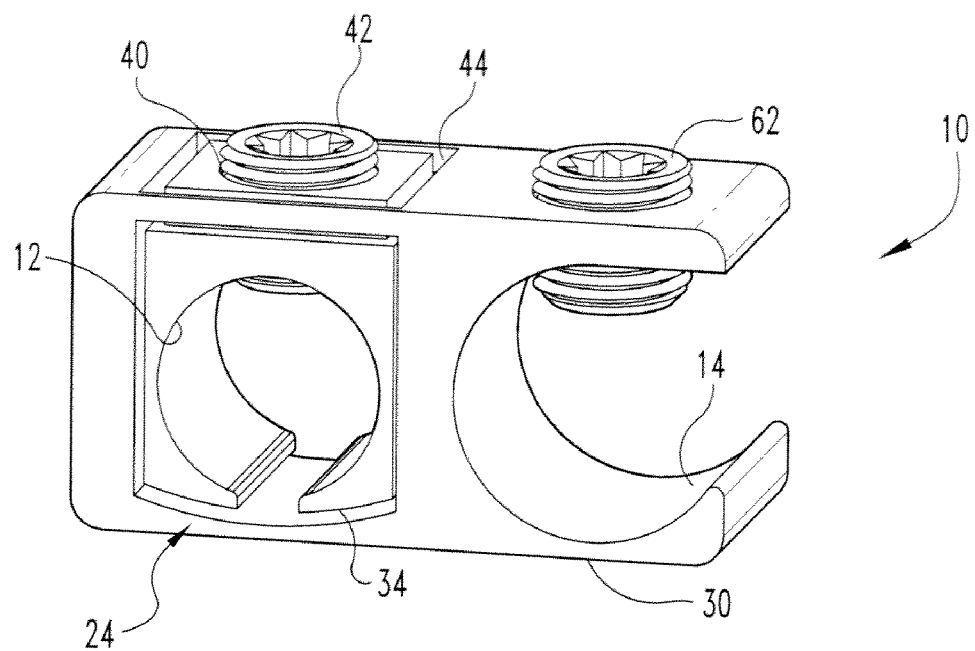
FIG. 1 is a perspective of a connector of one embodiment of the present invention having a closed passage including a variable angle mechanism for receiving a linkage member and an open lateral groove to receive a linkage member.

Referring now to the drawings and in particular FIG. 1, a first embodiment of a connector of the present invention is designated in its entirety by the reference number 10. The connector 10 includes a closed passage or opening 12 for receiving a first spinal linkage member (designated 20 in FIG. 2) and an open lateral groove or slot or opening 14 for receiving a second spinal linkage member (designated 22 in FIG. 2). The connector 10 may be used adjacent all areas of the spine.

Figure 2:
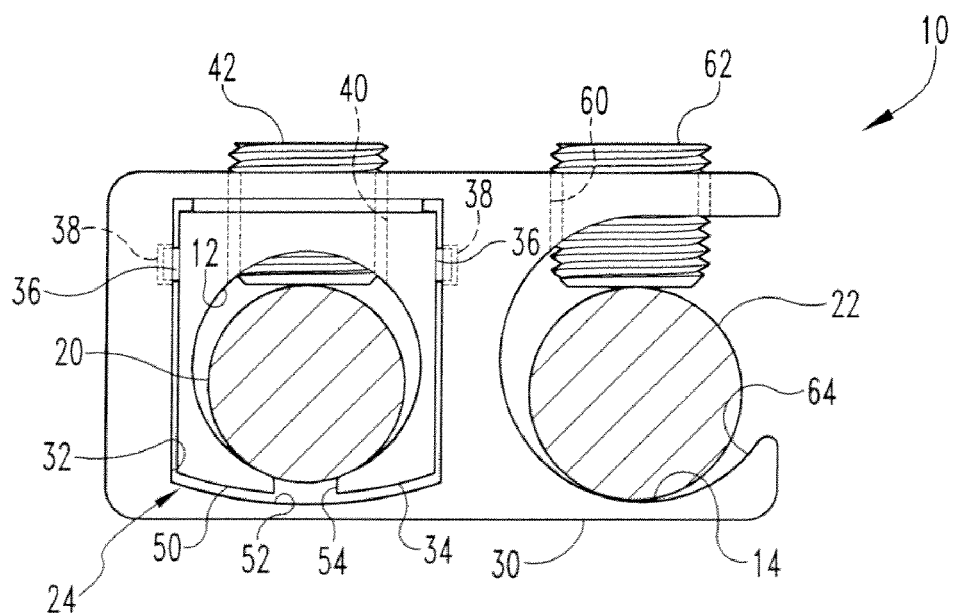
FIG. 2 is a top plan of the connector shown in FIG. 1 connecting two linkage members.
Figure 3:
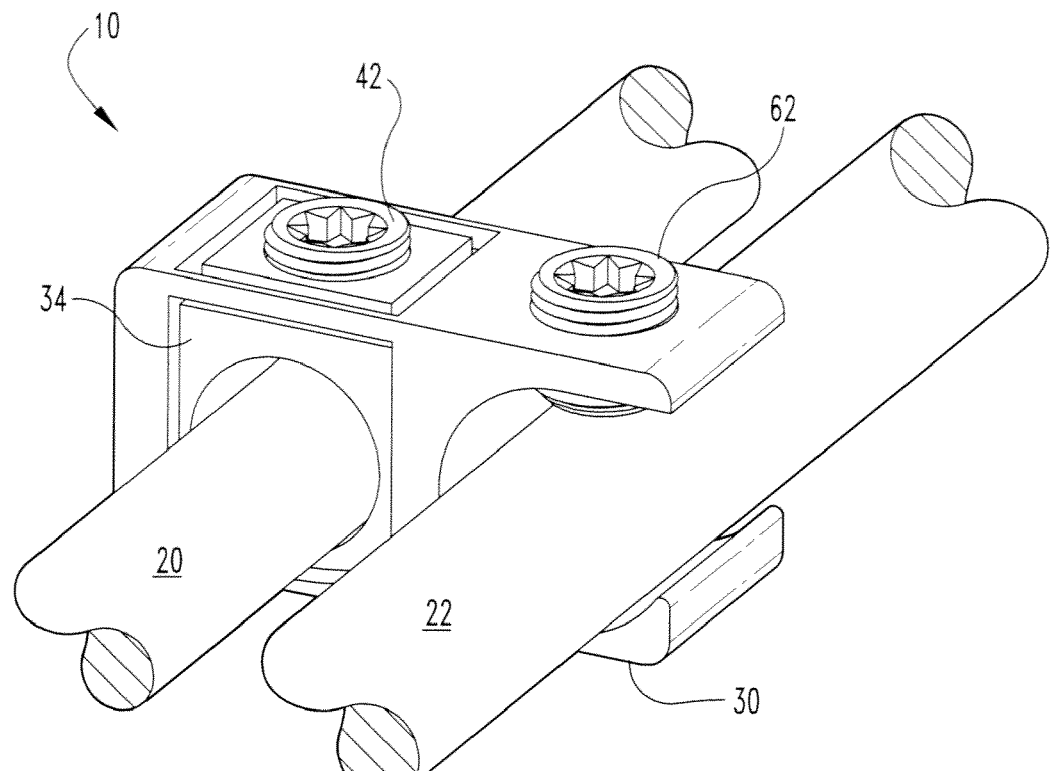
FIG. 3 is a perspective of the connector connecting two linkage members.

FIG. 2 illustrates a top plan of the connector 10. The connector 10 includes a closed passage 12 having a variable angle mechanism, generally designated by 24, for receiving a spinal linkage member (e.g., member 20) and an open lateral groove 14 for receiving another linkage member (e.g., member 22) according to one embodiment of the invention. The connector 10 has a body 30 having an opening 32 sized and shaped for receiving the variable angle mechanism 24. The mechanism 24 includes a housing 34 that is pivotally mounted in the opening 32 on axles formed by pins 36 rotatably mounted in recesses 38 in the body 30. The housing 34 has the closed passage 12 through which the spinal linkage member 20 is passed. A threaded hole 40 extends through the housing 34 intersecting the passage 12 generally perpendicular to the passage. A fastener such as a setscrew 42 is inserted into the threaded hole 40 for securing the connector 10 to the spinal linkage member 20 received in the closed passage 12. As shown in FIG. 3, the connector body 30 includes an opening 44 for accessing the fastener 42 to tighten the fastener once the connector 10 is in place.

Figure 4:
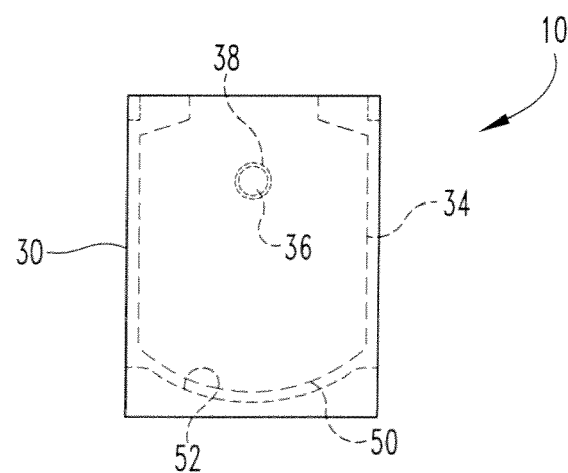
FIG. 4 is a side elevation of the connector shown in FIG. 1.

As illustrated in FIGS. 2 and 4, at least one surface 50 of the housing 34 and a corresponding surface 52 of the connector body 30 are spherical. Further, the pins 36 are smaller (both shorter and narrower) than the recesses 38, allowing the housing 34 to pivot in any direction within the body 30. The housing 34 includes a slot 54 that extends from the surface 50 to the closed passage 12. As the fastener 42 is tightened, the linkage member 20 presses against the slot 54 so the slots spreads open. As the slot 54 spreads, the corresponding spherical surfaces 50, 52 of the housing 34 and body 30 frictionally engage to prevent the housing from moving in the body. Thus, as the fastener 42 is tightened, the spinal linkage member 20 is locked in place in the closed passage 12 and the housing 34 is locked in place in the body 30.

The open groove or slot 14 in the body 30 receives the second spinal linkage member 22. A threaded hole 60 extends through the body 30 and intersects the passage 14 generally perpendicular to the passage. A fastener such as a setscrew 62 is inserted into the threaded hole 60 for securing the connector 10 to the spinal linkage member 22 received in the open groove 14. In one embodiment, the groove 14 includes a hooked lip 64 which ensures the spinal linkage member 22 is retained in the groove when the fastener 62 is tightened to firmly lock of the member in place in to the body 30 of the connector 10. Although the slot 14 faces laterally in the illustrated embodiment, those skilled in the art will appreciate that the slot may have alternative orientations without departing from the scope of the present invention.

Figure 5:
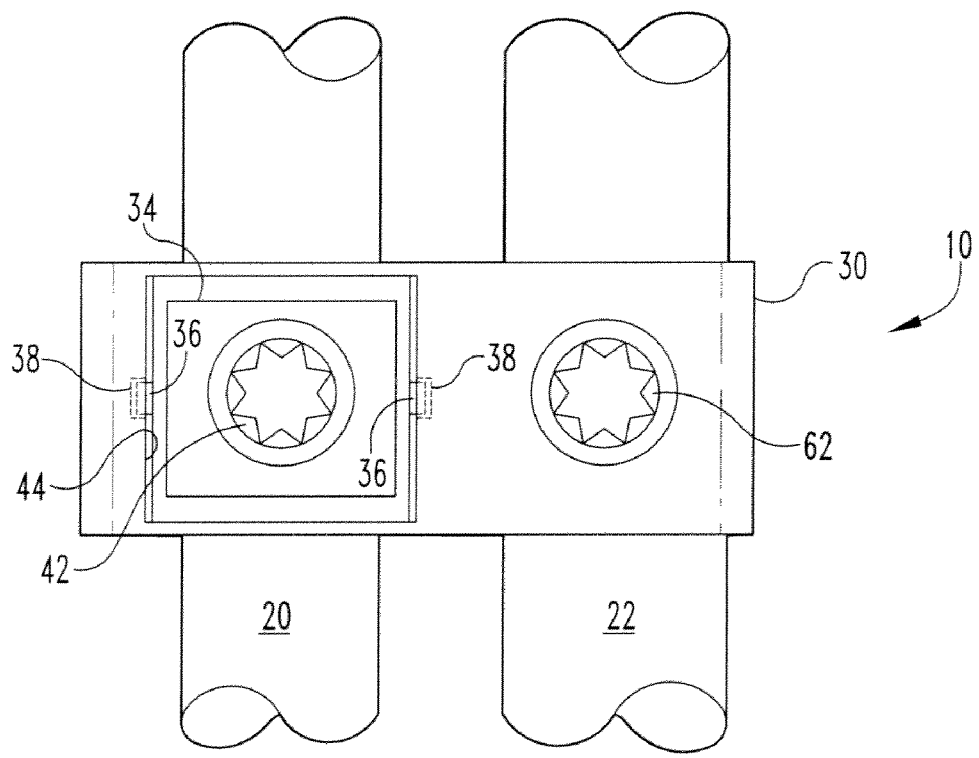
FIG. 5 is a rear elevation of the connector connected two linkage members.

FIG. 5 shows the connector 10 with both spinal linkage members 20, 22 seated in the body 30. As will be apparent to those skilled in the art, the selectively pivotable nature of the variable angle mechanism 24 allows the spinal linkage members 20, 22 to be angled relative to each other. Further, once the connector 10 accepts the spinal linkage members 20, 22, the fasteners 42, 62 are tightened to lock the connector in position on the members and the members in position relative to one another.

Figure 6:
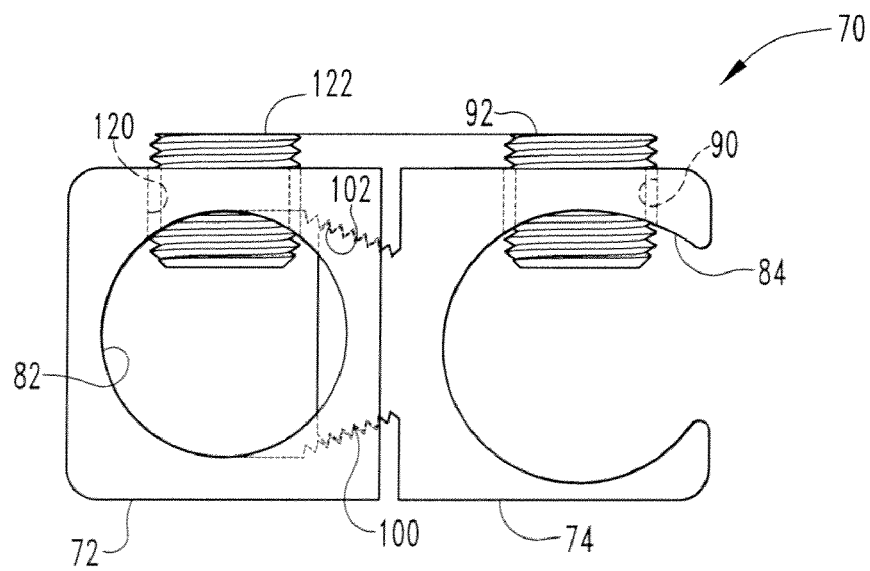
FIG. 6 is a top plan of a connector of a second embodiment of the present invention having a closed passage including a variable angle mechanism for receiving a linkage member and an open lateral groove to receive a linkage member.

FIG. 6 illustrates another embodiment of a connector of the present invention, generally designated in its entirety by the reference number 70. The connector 70 of the this embodiment includes a body constructed in two pieces 72, 74. The first piece 72 includes a closed passage 82 for receiving a first spinal linkage member (designated 20 in FIG. 7) and the second piece 74 includes an open lateral groove or slot 84 for receiving a second spinal linkage member (designated 22 in FIG. 7). The slot 84 of connector 70 of the second embodiment is substantially identical to the slot 14 of the first embodiment. A threaded hole 90 similar to hole 60 of the first embodiment extends through the piece 74 and intersects the passage 84 generally perpendicular to the passage. A fastener such as a setscrew 92 is inserted into the threaded hole 90 for securing the connector 70 to the spinal linkage member 22 received in the open groove 84. As the open lateral groove 84 is similar to the slot 14 in the connector 10 of the first embodiment, it will not be described in further detail.

As further illustrated in FIG. 6, the second piece 74 includes a post 100 extending generally perpendicular to both the threaded hole 90 and the slot 84. The first piece 72 has an opening 102 having a shape that complements the post 100. The post 100 is sized relative to the opening 102 to permit the first piece 72 and second piece 74 to move relative to each other. Although the post 100 and opening 102 may have other shapes without departing from the scope of the present invention, in one embodiment both the post and opening have generally conical shapes. It is envisioned that the post and opening may have generally spherical shapes in an alternate embodiment (not shown). In the illustrated embodiment, both the post 100 and the opening 102 include ridges and grooves to improve gripping between surfaces when they are engaged. In an alternate embodiment (not shown), it is envisioned that the surfaces may have other treatments (e.g., grit blasting or knurling) to improve gripping during engagement.

A threaded hole 120 extends through the first piece 72 and intersects the closed passage 82 generally perpendicular to the passage. A fastener such as a setscrew 122 is inserted into the threaded hole 120 for securing the first piece 72 to the spinal linkage member 20 received in the closed passage 82. As the fastener 122 is tightened, the linkage member 20 presses against the post 100 and forces it to seat in the opening 102. When the post 100 seats in the opening 102, the corresponding conical surfaces of the post and opening frictionally engage to prevent the first and second pieces 72, 74 of the connector 70 from moving relative to each other. Thus, as the fastener 122 is tightened, the spinal linkage member 20 is locked in place in the closed passage 82 and the first and second pieces of the connector 70 are locked in place.

Figure 7:
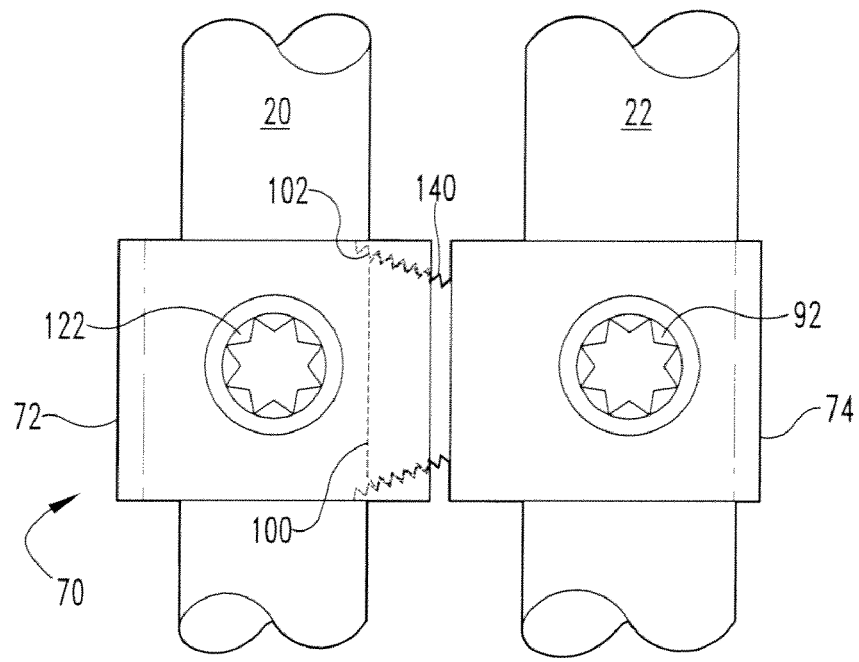
FIG. 7 is a rear elevation of the connector of the second embodiment connecting two linkage members.

FIG. 7 shows the connector 70 with both spinal linkage members 20, 22 seated in the body 80 and the halves of the body immobilized relative to each other. As will be apparent to those skilled in the art, the post 100 and opening 102 of the first and second pieces 72, 74 form a variable angle mechanism 140 of a second embodiment that allows the spinal linkage members 20, 22 to be angled relative to each other. Further, once the connector 70 accepts the spinal linkage members 20, 22, the fasteners 92, 122 are tightened to lock the connector in position on the members and the members in position relative to one another.

As will be appreciated by those skilled in the art, the spinal linkage members may extend at any suitable angle within a predetermined range of angles to accommodate a particular configuration of spinal instrumentation and spinal alignment.

The sizes of the closed passages and the open grooves that accommodate the spinal linkage members are selected so the linkage members can move laterally in the corresponding passage and groove. In one embodiment, the radii of the passages and grooves vary around their circumferences so that the radii at positions opposite the fasteners are approximately equal to or small than those of the linkage members to improve engagement between the connectors and members. One skilled in the art will recognize that the shape and size of the passages and grooves are not limited to the illustrated embodiments, and that any suitable size and/or shape, as well as relative location in the connector is envisioned.

According to an alternate embodiment, a locking mechanism for securing the position of the rods within the connector may comprise a plurality of setscrews. For example, the locking mechanism may comprise a first screw and a second screw disposed around the closed passage for the first linkage member for locking the connector components together and fixing the angular relation of the spinal linkage member relative to the body.

The present invention provides an improved connector for a spinal fixation system intended for connecting a first spinal linkage member to a second spinal linkage member. The connector provides an angled or non-parallel connection between the linkage members allowing for desired alignment or angular variation between portions of the spinal fixation system. The connector may include a first passage for receiving a portion of the first spinal linkage member, and a groove or slot for receiving a portion of the second spinal linkage member. Thus, the orientation of the first linkage member may vary relative to the second linkage member. The connector may comprise a variable connection mechanism functionally separating the passage of the first member and the groove of the second member. The variable connection mechanism may include a swivel type joint and surface treatments to reliably lock angular offset between portions of the connector and thus the angle between the linkage members.

The invention will be described relative to illustrative embodiments, though one skilled in the art will recognize that the invention is not limited to the described embodiments. While the connector may be primarily applied in spinal surgery, the connector may also be employed to couple any type of components of an implant system. The material composition of the connector and its components may be formed of any suitable bio-compatible material, including, but not limited to stainless steel, titanium, nitinol, metal alloys, plastic, polymers, carbon based materials, ceramics, and mixtures or combinations thereof.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A spinal fixation system connector for maintaining a predetermined position of a first spinal linkage member fastened to vertebrae of a patient to a second spinal linkage member fastened to vertebrae of the patient, said connector comprising:
   a body having a first opening extending through the body, a housing movably mounted within said first opening and including a passage extending through said housing along a first axis and sized and shaped for receiving said first spinal linkage member, and a second opening extending through the body along a second axis and sized and shaped for receiving said second spinal linkage member;
   a first fastener for fastening the first spinal linkage member in said passage in said housing; and
   wherein prior to the first fastener fastening the first spinal linkage member in said passage in said housing, said housing is manipulatable within said first opening in said body to adjust an angle between said first axis and said second axis; and
   wherein the first fastener is engaged against the first spinal linkage member in said passage in said housing which engages a first surface of said housing against a second surface of said body to prevent further movement of said housing within said first opening in said body to thereby fix the angle between said first axis and said second axis.

2. A connector as set forth in claim 1 wherein the first opening comprises a closed passage.

3. A connector as set forth in claim 1 wherein the second opening comprises a lateral facing groove that opens laterally onto a side of said body.

4. A connector as set forth in claim 1 in combination with said first spinal linkage member and said second spinal linkage member.

5. A connector as set forth in claim 1 wherein said housing is pivotally mounted within said first opening in said body to allow pivotal movement of said housing within said first opening about a pivot axis;
   wherein prior to said first fastener fastening the first spinal linkage member in said first opening in the body, said housing is pivotable within said first opening to adjust said angle between said first axis and said second axis; and
   wherein said first fastener is engaged against the first spinal linkage member in said passage which engages said first surface of said housing against said second surface of said body to prevent further pivotal movement of said housing within said first opening in said body to thereby fix said angle between said first axis and said second axis.

6. A connector as set forth in claim 5 wherein said housing is pivotally mounted within said first opening in said body by a pivot member extending along said pivot axis.

7. A connector as set forth in claim 6 wherein said pivot member comprises axial pin portions extending from said housing, said pin portions positioned within recesses formed in said body.

8. A connector as set forth in claim 5 wherein said first surface of said housing and said second surface of said body have complementary curved configurations.

9. A connector as set forth in claim 8 wherein said first surface of said housing and said second surface of said body have complementary spherical configurations.

10. A connector as set forth in claim 1 wherein said housing includes a slot extending from said first surface to said passage; and wherein said slot opens as said first fastener is engaged against the first spinal linkage member in said passage which engages said first surface of said housing against said second surface of said body to prevent further movement of said housing within said first opening in said body.

11. A connector as set forth in claim 1 wherein said first fastener is mounted on said housing.

12. A connector as set forth in claim 11 wherein said first fastener is threadedly engaged within a threaded opening in said housing.

13. A connector as set forth in claim 1 further comprising a second fastener mounted on said body for fastening the second spinal linkage member in said second opening of said body.

14. A connector as set forth in claim 1 wherein said passage in said housing comprises a closed passage extending substantially entirely about the first spinal linkage member.

15. A connector as set forth in claim 1 wherein said body comprises a unitary, single-piece connector body.

16. A connector as set forth in claim 1 wherein said first and second openings in said body remain in a fixed position and orientation relative to one another as said housing is manipulated within said first opening to adjust said angle between said first axis and said second axis.

17. A spinal fixation system connector for maintaining a predetermined position of a first spinal linkage member fastened to vertebrae of a patient to a second spinal linkage member fastened to vertebrae of the patient, said connector comprising:
a body comprising a first piece and a second piece, and a variable angle mechanism connecting said first piece to said second piece, said first piece defining a first opening extending therethrough along a first axis and sized and shaped for receiving the first spinal linkage member, said second piece defining a second opening extending therethrough along a second axis and sized and shaped for receiving the second spinal linkage member, said variable angle mechanism comprising a third opening extending into said first piece and a post extending laterally from said second piece along a pivot axis, said post engaged within said third opening to thereby allow said first piece to pivot relative to said second piece about said pivot axis to adjust an angle between said first axis and said second axis; and
a first fastener mounted on said first piece of the body for fastening the first spinal linkage member in said first opening;
a second fastener mounted on said second piece of the body for fastening the second spinal linkage member in said second opening; and
wherein said first fastener is engaged against the first spinal linkage member and presses the first spinal linkage member against said post to displace said post in a lateral direction along said pivot axis to engage a first laterally facing surface of said post against a second laterally facing surface of said opening to thereby prevent further pivotal movement of said first piece relative to said second piece and fix said angle between said first axis and said second axis.

18. A connector as set forth in claim 17 wherein said first and second laterally facing surfaces have complementary conical shapes.

19. A connector as set forth in claim 17 wherein said first and second laterally facing surfaces include gripping elements that facilitate frictional engagement between said first and second laterally facing surfaces to prevent further pivotal movement of said first piece relative to said second piece.

20. A spinal fixation system connector for maintaining a predetermined position of a first spinal linkage member fastened to vertebrae of a patient to a second spinal linkage member fastened to vertebrae of the patient, said connector comprising:
a body having a first opening extending through the body along a first axis, said first opening being sized and shaped for receiving said first spinal linkage member, and a second opening extending through the body along a second axis, said second opening being sized and shaped for receiving said second spinal linkage member;
a first fastener mounted on the body for fastening the first spinal linkage member in said first opening of the body; and
a second fastener mounted on the body for fastening the second spinal linkage member in said second opening of the body;
wherein prior to the first fastener fastening the first spinal linkage member in said first opening of the body and the second fastener fastening the second spinal linkage member in said second opening of the body, the body is manipulatable to adjust an angle between said first axis and said second axis;
wherein the first fastener is engaged against the first spinal linkage member in said first opening of the body and the second fastener is engaged against the second spinal linkage member in said second opening of the body to thereby fix the angle between said first axis and said second axis;
wherein the body comprises a first piece and a second piece, and a variable angle mechanism connecting said first piece to said second piece, the variable angle mechanism is positioned between said first spinal linkage member and said second spinal linkage member, the variable angle mechanism includes an opening extending into said first body piece and a post extending from said second body piece for engaging the opening of said first body piece, the opening extending into said first body piece intersects the first opening in the body so that when the first spinal linkage member is positioned in the first opening of the body and the first fastener fastens the first spinal linkage member in said first opening of the body, the first spinal linkage member engages the post of said second body piece thereby causing the post to engage the opening extending into said first body piece to fix the angle between said first axis and said second axis; and
wherein the opening extending into said first body piece and the post extending from said second body piece have corresponding complementary conical shapes.

21. A spinal fixation system connector for maintaining a predetermined position of a first spinal linkage member fastened to vertebrae of a patient to a second spinal linkage member fastened to vertebrae of the patient, said connector comprising:
a body having a first opening extending through the body along a first axis, said first opening being sized and shaped for receiving said first spinal linkage member, and a second opening extending through the body along a second axis, said second opening being sized and shaped for receiving said second spinal linkage member,
a first fastener mounted on the body for fastening the first spinal linkage member in said first opening of the body; and a second fastener mounted on the body for fastening the second spinal linkage member in said second opening of the body;

wherein prior to the first fastener fastening the first spinal linkage member in said first opening of the body and the second fastener fastening the second spinal linkage member in said second opening of the body, the body is manipulatable to adjust an angle between said first axis and said second axis;

wherein the first fastener is engaged against the first spinal linkage member in said first opening of the body and the second fastener is engaged against the second spinal linkage member in said second opening of the body to thereby fix the angle between said first axis and said second axis;

wherein the body comprises a first piece and a second piece, and a variable angle mechanism connecting said first piece to said second piece, the variable angle mechanism is positioned between said first spinal linkage member and said second spinal linkage member;

wherein the first piece of the body includes an opening sized and shaped for receiving the second piece of the body, the second piece is connected to the first piece by an axle allowing pivotal movement between the first piece and the second piece; and wherein the second piece includes a slot that opens as the first fastener fastens the first spinal linkage member in the first opening of the body.

22. A connector as set forth in claim 21 wherein:
the first piece and the second piece include corresponding surfaces having complementary spherical shapes; and
the corresponding spherical surfaces engage each other as the slot opens.

23. A surgical system for maintaining a predetermined position of vertebrae of a patient, said system comprising:
a first elongate spinal linkage member;
a first anchor for attaching the first member to a first vertebra;
a second elongate spinal linkage member;
a second anchor for attaching the second member to a second vertebra; and
a connector including:
a body having a first opening extending through the body, a housing pivotally mounted within said first opening and including a passage extending through said housing along a first axis with said first spinal linkage member positioned within said passage, and a second opening extending through the body along a second axis with said second spinal linkage member positioned within said second opening;
a first fastener mounted on said housing for fastening the first spinal linkage member in said passage in said housing; and
a second fastener mounted on the body for fastening the second spinal linkage member in said second opening of the body;

wherein prior to the first fastener fastening the first spinal linkage member in said passage in said housing, said housing is pivotable within said first opening in said body to adjust an angle between said first axis and said second axis; and wherein the first fastener is engaged against the first spinal linkage member in said passage in said housing which prevents further pivotal movement of said housing within said first opening in said body to thereby fix the angle between said first axis and said second axis.

24. A system as set forth in claim 23 wherein when said first fastener is engaged against said first spinal linkage member in said passage in said housing, a first surface of said housing is engaged against a second surface of said body to prevent further pivotal movement of said housing within said first opening in said body to thereby fix said angle between said first axis and said second axis.

25. A system as set forth in claim 23 wherein said housing includes a slot that opens as said first fastener is engaged against said first elongate spinal linkage member in said passage.

26. A system as set forth in claim 25 wherein opening of said slot engages a first surface of said housing against a second surface of said body to prevent further pivotal movement of said housing within said first opening in said body to thereby fix said angle between said first axis and said second axis.

27. A system as set forth in claim 23 wherein said first fastener is threadedly engaged within a threaded opening in said housing.

28. A system as set forth in claim 23 wherein said body comprises a unitary, single-piece connector body.

29. A system as set forth in claim 23 wherein said first and second openings in said body remain in a fixed position and orientation relative to one another as said housing is pivoted within said first opening to adjust said angle between said first axis and said second axis.

* * * * *